United States Patent [19]

Reinert et al.

[11] Patent Number: 4,655,785

[45] Date of Patent: Apr. 7, 1987

[54] PROCESS FOR PHOTOCHEMICAL STABILIZATION OF POLYAMIDE AND POLYURETHANE FIBER MATERIALS WITH METAL COMPLEX COMPOUNDS

[75] Inventors: Gerhard Reinert, Allschwil, Switzerland; Gerhard Back, Lörrach, Fed. Rep. of Germany; Helmut Huber-Emden, Schönenbuch, Switzerland

[73] Assignee: Ciba-Geigy Corporation, Ardsley, N.Y.

[21] Appl. No.: 736,927

[22] Filed: May 21, 1985

[30] Foreign Application Priority Data

May 22, 1984 [CH] Switzerland ................. 2509/84

[51] Int. Cl.$^4$ ................. D06P 1/64; D06P 3/24; D06M 13/50
[52] U.S. Cl. ................. 8/442; 8/602; 8/605; 8/623; 8/624; 8/628; 8/924; 8/926; 556/33; 556/34
[58] Field of Search ............ 8/442, 602, 605, 624, 8/628, 623

[56] References Cited

U.S. PATENT DOCUMENTS

| | | | |
|---|---|---|---|
| 3,203,752 | 8/1965 | Mills et al. | 8/551 |
| 3,226,178 | 12/1965 | Walker | 8/598 |
| 3,361,710 | 1/1968 | Sparks | 524/204 |
| 4,253,843 | 3/1981 | Bannisaw | 8/624 |
| 4,383,835 | 5/1983 | Preuss et al. | 8/602 |

FOREIGN PATENT DOCUMENTS 2146357 4/1985 United Kingdom .

*Primary Examiner*—A. Lionel Clingman
*Attorney, Agent, or Firm*—Edward McC. Roberts; Meredith C. Findlay; Irving M. Fishman

[57] ABSTRACT

A process for the photochemical stabilization of undyed and dyed polyamide or polyurethane fibre material that is characterized in that the fibre material is treated with a water soluble, organic copper, manganese or nickel complex that displays an affinity for the fibres. The polyamide or polyurethane fibre material, e.g., textile, that has been so treated retains its stretch characteristics and elasticity even after prolonged periods of illumination. In addition, in the case of dyed material, treatment with the metal complex results in a marked improvement in light-fastness.

9 Claims, No Drawings

PROCESS FOR PHOTOCHEMICAL STABILIZATION OF POLYAMIDE AND POLYURETHANE FIBER MATERIALS WITH METAL COMPLEX COMPOUNDS

The present invention relates to a process for the photochemical stabilisation of undyed and dyed polyamide fibre material and mixtures of these with other fibres, and to the fibre material, stabilized against photochemical breakdown and/or bleaching of the colour, as such. The invention also relates to water-soluble copper, manganese, and nickel complexes of bisazomethines, acylhydrazones, semicarbazones and thiosemicarbazones of aromatic aldehydes and ketones.

The use of copper salts such as, for example, copper sulfate, in order to improve the light-fastness of dyes on polyamide fibres with metal complex dyes is generally known; reference is made to the article by I. B. Hanes in ADR 3 (1980), pp. 19 and 20. However, in many instances, inorganic or even organic copper salts entail the disadvantage that they attach themselves insufficiently and unevenly to the polyamide fibres, and for this reason have to be used in high concentrations in order to achieve the desired effect.

For this reason, attempts have been made to use the copper in the form of compounds that display an affinity for polyamide fibres. Thus, for example, EP No. 00 18 775 recommends copper phosphate that behaves in a manner similar to a dispersion dye and attaches itself correspondingly to nylon fibres. Copper compounds of this kind, that display an affinity to fibres are generally of poor water solubility, and this has a negative effect on the degree of attachment. Furthermore, the copper that remains behind in the dye vat pollutes the waste water that is produced.

This problem can be solved in that instead of the familiar copper compounds that have either a reduced affinity for fibres or are difficult to dissolve in water, use is made of organic copper, manganese or nickel complexes that display an affinity for fibres and dissolve easily in water.

Thus, the object of the present invention is a process for the photochemical stabilization of dyed and undyed materials of polyamide fibres, and mixtures of these with other fibres, that is characterized in that the fibre material is treated with an organic and water-soluble copper, manganese or nickel complex that displays an affinity for fibres. It is of course understood that only those complexes that are for all practical purposes colourless or are only slightly coloured are considered for this purpose.

In the present document, the expression "photochemical stabilisation" relates both to light-fastness, in the event that undyed material is involved, as well as to the preservation of the mechanical properties of the undyed and the dyed polyamide or polyurethane fibres. The wording "dyed polyamide or polyurethane material" is taken to include optically brightened fibre material.

Especially good results are obtained by using copper, manganese, and nickel complexes of bisazomethines, acylhydrazones, semicarbazones and thiosemicarbazones of the aromatic aldehydes or ketones that contain sulfur groups. Compounds of these kinds dissolve readily in water and, in addition to this, display an excellent affinity to polyamide or polyurethane fibres. For this reason, such compounds are already effective in small quantities. In addition, it has been found that they not only increase the light-fastness of the dyed polyamide or polyurethane material, but also protect the polyamide or polyurethane fibres in general against photochemical breakdown and thus, to a very great extent, preserve their mechanical properties such as rip resistance and elasticity.

In this specification, bisazomethines of aromatic aldehydes and ketones are taken to refer to the Schiff bases of aliphatic or aromatic diamines, the aldehydes and ketones having an OH group in the o-position to the formyl or acyl group. The bond with the metal atom is through these two OH groups and the two nitrogen atoms in the bisazomethine section. Thus, four-bond ligands are involved. The ligands contain one or even several sulfogroups that are located in the aldehyde or ketone sections and/or in the bisazomethine bridge.

Bisazomethine-metal complexes of formula I are preferred for use;

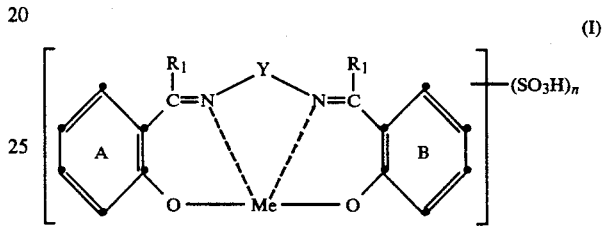

(I)

wherein $R_1$ stands for hydrogen or an optionally substituted alkyl or aryl group, Y is an optionally substituted alkylene or arylene group, and Me stands for copper, manganese or nickel, and $n = 1$ to 3. The benzene rings A and B can be substituted in the same way, even independently of each other.

If $R_1$ stands for an optionally substituted alkyl group, it is preferred that a $C_1$ to $C_8$ alkyl group, in particular a $C_1$ to $C_4$ alkyl group is involved; this can be branched or straight and optionally substituted, by a halogen such as fluorine, chlorine or bromine, $C_1$ to $C_4$ alkoxy such as methoxy or ethoxy, by a phenyl or carboxyl group, by $C_1$ to $C_4$ alkoxycarbonyl, such as, for example, the acetyl group or by hydroxy or a mono- or dialkyl amino group. Furthermore, the cyclohexyl group can also be suitable; this too can be optionally substituted, for example, by $C_1$ to $C_4$-alkyl or $C_1$ to $C_4$-alkoxy.

If $R_1$ stands for an optionally substituted aryl group, a phenyl or naphthyl group can be considered; this can be substituted by a $C_1$ to $C_4$ alkyl such as methyl, ethyl, propyl, isopropyl, butyl, isobutyl, secondary butyl or tertiary butyl, $C_1$–$C_4$-alkoxy, such as methoxy, ethoxy, propoxy, isopropoxy, butoxy, isobutoxy, secondary butoxy and tertiary butoxy, halogen, such as fluorine, chlorine, bromine; $C_2$–$C_5$-alkanoylamino, such as acetylamino, propionylamino and butyrylamino, nitro, cyano, sulfo or a mono or dialkyl amino group.

If Y stands for an alkylene group, this involves principally a $C_2$ to $C_4$ alkylene group, in particular a —CH$_2$—CH$_2$ bridge. However, also suitable is a $C_2$ to $C_8$ alkylene chain interrupted by oxygen or in particular by nitrogen, preferably the —(CH$_2$)$_3$—NH—(CH$_2$)$_3$- bridge.

If Y stands for an arylene group, this will in the first place be a phenylene group, particularly an o-phenylene group. This can also be substituted by $C_1$ to $C_4$ alkyl or $C_1$ to $C_4$ alkoxy.

The following can be considered as substituents for the A and B benzene rings: $C_1$ to $C_4$ alkyl, $C_1$ to $C_4$ alkoxy, halogens such as fluorine, chlorine or bromine, and the cyano- or nitro-groups.

The sulfo groups that are located in the A and/or B benzene rings and/or in the bridge member Y, in the event that Y stands for an aryl group, are present, preferably, as alkali metal salts, in particular as the sodium salt, or as amine salts.

It is, in particular, the copper complexes of formula I that are used in the present process, wherein $R_1$ stands for hydrogen, Y stands for the ethylene or o-phenylene bridge, and $n=2$, the two sulfo groups being in the A and B benzene rings and principally the complexes in which the sulfo groups are in each instance arranged para to the oxygen.

In the copper, manganese, and nickel complexes of the acylhydrazones of aromatic aldehydes and ketones what is involved are principally the complexes of formula II

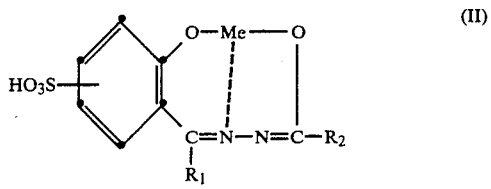
(II)

wherein $R_1$ is as described for Formula I and $R_2$ stands for hydrogen or an optionally substituted alkyl- or aryl group. Once again, Me stands for copper, manganese, or nickel.

Should $R_2$ stand for an alkyl group, this can be either branched or straight and have a chain length of 1 to 8, preferably 1 to 4 C atoms. Halogens such as fluorine, chlorine or bromine, $C_1$ to $C_4$-alkoxy, such as methoxy or ethoxy, in addition, phenyl or carboxyl, $C_1$ to $C_4$ alkoxycarbonyl, such as acetyl or hydroxy, mono- or dialkylamino can be considered as substituents.

If $R_2$ stands for an optionally substituted aryl group, a phenyl- or napthyl group can be considered, and this can be substituted by $C_{1-4}$-alkyl, such as methyl, ethyl, propyl, isopropyl, butyl, isobutyl, secondary butyl and tertiary butyl, $C_{1-4}$-alkoxy, such as methoxy, ethoxy, propoxy, isoproxy, butoxy, isobutoxy, secondary butoxy and tertiary butoxy, halogens such as fluorine, chlorine and bromine, $C_{2-5}$-alkanoylamino, such as acetylamino, propionylamino and butyrylamino, nitro, cyano, sulfo or a mono- or dialkyl amino group.

It is also preferred that the complexes of Formula II be used in neutral form, i.e., as alkali salts, in particular the sodium salt or an amine salt.

Preferred for use are those complexes of Formula II in which $R_1$ and $R_2$ stand for hydrogen, methyl or in particular the phenyl group, and which contain copper as the metal, above all the complexes in which the sulfo group is once again in the p-position to the oxygen.

By copper, manganese, and nickel complexes of semicarbazones or thiosemicarbazones are primarily intended complexes of Formula III

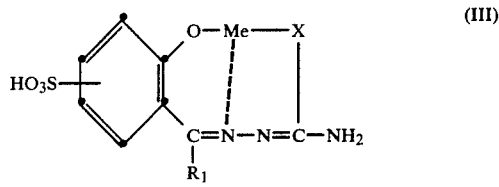
(III)

wherein $R_1$ is of the value cited in connection with Formula I, and X stands for oxygen or sulfur. Me indicates copper, manganese or nickel. It is also preferred that the complexes of Formula III be used as alkali salts, in particular the sodium salt or an amine salt.

In addition to the transition metal complexes of Formulae II and III, the ligands of which derive from the sulfosalicylaldehyde or the corresponding phenyl ketones, suitable metal complexes are also those in which, instead of mononuclear aromatic aldehydes and ketones, polynuclear aromatic aldehydes and ketones such as the 2-hydroxy-1-naphthaldehyde sulfonic acids, are used to synthesize the ligand. Furthermore, reference is also made to the fact that the fourth coordination position of the metal atom in the complexes of Formulae II and III is occupied by water as a neutral ligand.

In the present process, it is preferred that in particular the copper complexes of Formulae I and II be used for the photochemical stabilization.

The water soluble metal complexes that display an affinity to fibres are most effectively applied in a water bath and are best used in such a quantity that 5 to 200 μg, in particular 10 to 100 μg of metal and applied to each g of polyamide or polyurethane fibre material. When copper compounds are used, the optimal results are achieved with quantities of 10 to 50 μg of metal per g of polyamide or polyurethane material, and in the case of manganes complexes, with quantities of 10 to 100 μg of metal per g of polyamide or polyurethane material.

If the metal complexes are used for stabilizing dyed material, the fibre material can be treated with the metal complex prior to, during, or subsequent to the dyeing process. It is most effective if the metal complex be added directly to the dye bath. Dyeing can be carried out continuously or discontinuously.

Polyamide material is taken to mean synthetic polyamide, for example, polyamide-6, polyamide-66 or polyamide-12. In addition to the pure polyamide fibres, fibre mixtures of polyurethane and polyamide can also be considered, such material being, for example, tricot material of polyamide/polyurethane mixed at a ratio of 70:30. Basically, the pure or the mixed polyamide material can be in the most varied processing forms, such as fibre, yarn, woven textiles, and the like.

The dyeing process is carried out in the conventional manner, for example, with metal-complex dyestuffs or with acid dyes. Familiar types, in particular the 1:2 chromium or 1:2 cobalt complexes of mono- or disazo dystuffs are used as metal-complex dyestuffs; a large number of these are described in the literature. In addition to these, there are of course the dyestuffs of other classes such as dispersion or vat dyestuffs.

A further object of the present invention are the copper, manganese and nickel complexes of Formulae I, II and III and their alkali metal salts such as the potassium and lithium salts and in particular their sodium salts. These are obtained by known methods.

The metal complexes of Formula I are obtainable, for example, by two methods. In the first instance, one can first metallize the aldehyde or the ketone and then convert it to the finished complex of Formula I with the corresponding diamine. However, one can also first synthesize the ligands from aldehyde or ketone and diamine and then carry out the metallizing stage.

The introduction of the sulfo groups can take place at different stages of the synthesis. As an example, one can proceed from an o-hydroxyaldehyde or ketone that contains sulfo groups and then convert this to bisazomethine using a diamine—that can either contain sulfo groups or not—and then complete the metallizing stage. It is also possible to metallize an aldehyde or ketone that contains sulfo groups and then convert the metal complex to the bisazomethine-metal complex with a diamine. Finally, one can first produce the metal complex of the o-hydroxyaldehyde or ketone and then convert this to the corresponding bisazomethine-metal complex by way of conversion with a diamine that contains sulfo groups, for example, 3,4-diaminobenzene sulfonic acid.

The metallizing is carried out with copper hydroxide, for example, in that freshly precipitated copper hydroxide is added in at least equivalent quantities to an aqueous solution of the ligand, this is stirred until the conclusion of the complex-formation process, and then this is separated off from any excess of copper hydroxide.

It is preferred that one converts, in known manner, an o-hydroxyaldehyde that is free of sulfo groups or an o-hydroxyketone that is free of sulfo groups to bisazomethine using diamine, sulfonates this, and then metallizes it. Preferably, the sulfonation takes place in 5 to 50% oleum, in particular in 10 to 30% oleum, at 70° to 150° C., preferably 100° to 140° C.

It is preferred that the three steps set out above—formation of the bisazomethines, sulfonation, and metallization, are carried out as a single reaction, i.e., without any isolation of the intermediate stages.

The acylhydrazones, the ligands of the complex II are extracted, for example, by reaction of the aldehyde or ketone with the corresponding monoacylhydrazine and subsequent metallization. The complexes of Formula II can be produced in a similar manner.

The manganese and, above all, the copper complexes of Formulae I–III, in particular the copper complexes of the Formulae I and II, are preferred.

Within Group I (metal complexes with bisazomethine ligand) it is the copper complexes of the Formulae IV and V that are preferred

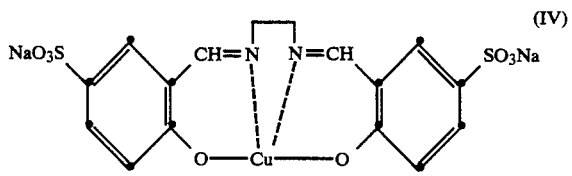
(IV)

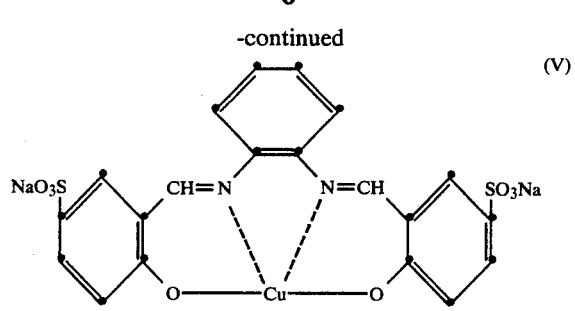
(V)

and within the Group III (metal complexes with acylhydrazone ligand) it is the copper complexes of the Formulae VI, VII and VIII that are preferred

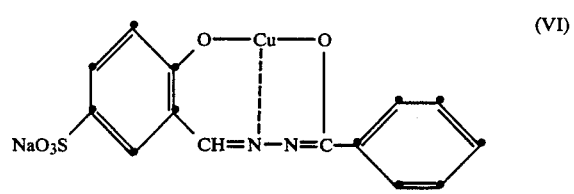
(VI)

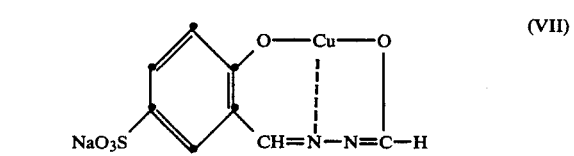
(VII)

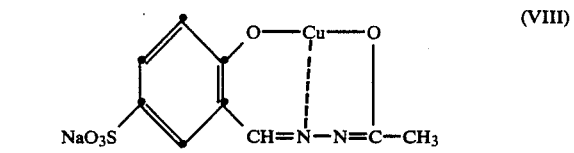
(VIII)

Within Group III the following compounds of the Formulae IX and X are especially preferred

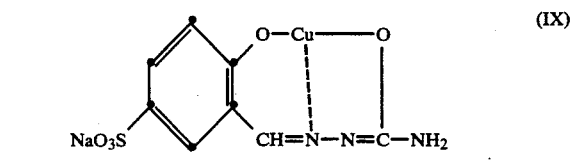
(IX)

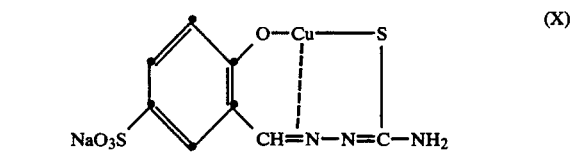
(X)

The fourth coordination location of the copper in the complexes of the Formulae VI, VII, and VIII is occupied by water, without this having any express effect on the structural formula.

The following examples serve to illustrate the invention. Parts refers to parts by weight, percentages refers to percentages by weight. With reference to the additions of the individual treatment or dyeing baths, the percentage data refer, unless otherwise noted, to the fibre material. Temperatures are in degrees Celsius.

EXAMPLE 1

Stabilization of the undyed polyamide material

Three 10 g yarn strands of polyamide-66 were treated in a dyeing apparatus (for example, a dyeing apparatus having open dyeing baths) with dye liquor (liquor ratio 1:20) that in general contain 2% ammonium sulfate (pH 6.5) and the following additives:

Dye bath (a): No additives.

Dye bath (b): 2.38 mg copper complex of Formula IV

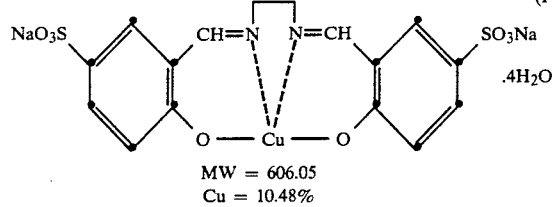

MW = 606.05
Cu = 10.48%

Dye bath (c): 1.6 mg copper complex of formula VI

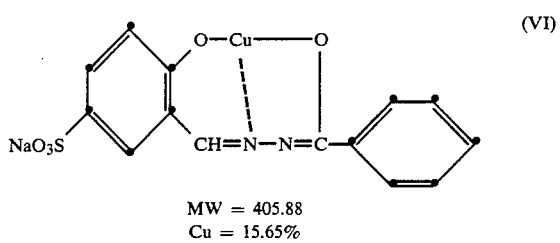

MW = 405.88
Cu = 15.65%

The fibre material was illuminated in a Fade-Ometer (Atlas Electric Devices, Co., Cicago) for 200 hours at a "black panel temperature" of 83° C. The yarn was then tested according to SNV 197.461 (Guidelines of the Swiss Standards Association) for break strength and stretch. The following results were obtained:

| Dyeing bath | Cu Content* μg/g | % | Break Resistance (%) | Stretch (%) |
|---|---|---|---|---|
| (a) | — | — | 23 | 32 |
| (b) | 23 | 0,0023 | 76,2 | 81,2 |
| (c) | 25 | 0,0025 | 81,6 | 84,9 |
| Blind treatment without illumination | — | — | 100 | 100 |

*according to microanalysis of the polyamide fibre material.

EXAMPLE 2

Improvement of the Light-fastness of a Beige Dye

Polyamide-6 tricot, previously washed as is customary, was treated as follows:

(a) Conventionally dyed

The dye bath was charged with 2% ammonium sulfate (pH 6.5) and the polyamide material was pre-rinsed for approximately 5 minutes at 40° C. This was followed by the addition of the following quantities of dye, dissolved in water (calculated in each instance on the basis of the fibre material):

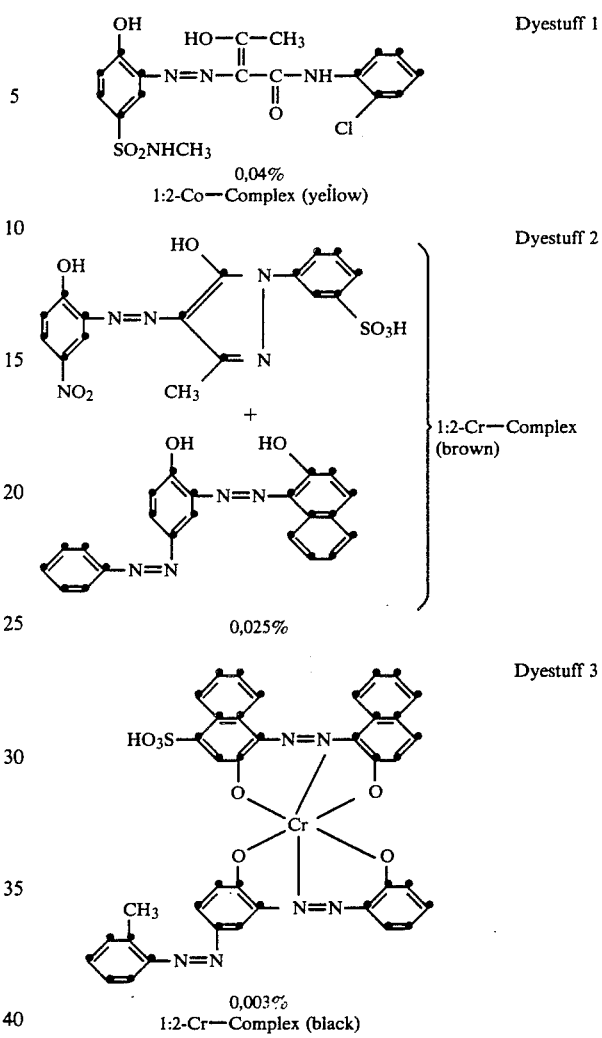

Next, the dye bath was heated to 95° C. at a rate of 1½° C. per minute and maintained at this temperature for 45 minutes. After a dyeing time of 10 minutes the pH value of the dye was adjusted to 5.2 by the additional of 80% acetic acid. Once the dyeing time has expired, the bath was allowed to a cool to 70° C., the dyed material removed, warm rinsed, centrifuged, and dried at 100° C.

(b) By the addition of Cu complexes having affinity to fibres.

The process as in paragraph (a) was repeated; however, at the beginning of the dyeing process 0.0238% of the complex of Formula IV, or in an additional dyeing process, 0.016% of the complex of Formula VI was added. The quantities of Cu complex of Formula IV or VI correspond to a theoretical quantity of Cu of 25 μg/g polyamide.

The tricot material, dyed as at (a) and (b) was tested for light fastness as laid down in SN-ISO 105-B02 (Xenon) and a provisional hot-illumination test as laid out in DIN 75.202 (Fakra).

Results:

| Dye Process | Light fastness | |
|---|---|---|
| | SNV 195.809 | Xenon Hot illumination |
| without Cu Complex | 5 | 4 |

| Dye Process | Light fastness | |
|---|---|---|
| | SNV 195.809 | Xenon Hot illumination |
| with Cu Complex IV | 6 | 6-7 |
| with Cu Complex VI | 5-6 | 6 |

EXAMPLE 3

Improvement of the light-fastness of a light olive dye

The dyeing process was carried out as described in Example 2, with the difference that the following dye combinations were used for colouring and the quantities of the additives of Cu-complex IV and VI were doubled (corresponds to a theoretical Cu quantity of 50 μg/g polyamide).

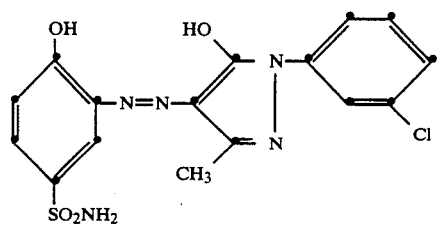

0,05% Dyestuff 4 — 1:2-Co—Complex (yellow)

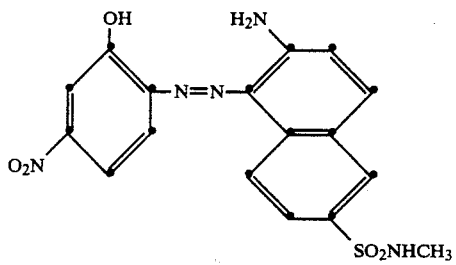

0,25% Dyestuff 5 — 1:2-Co—Complex (green)

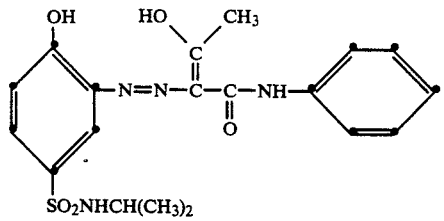

0,035% Dyestuff 3 — (black)

according to Example 2

The dyeing was tested as described for Example 2. The following results were obtained:

| Dye Process | Light fastness | |
|---|---|---|
| | SNV 195.809 | Xenon Hot illumination |
| without Cu Complex | 5 | 4 |
| with Cu Complex IV | 6+ | -6 |
| with Cu Complex VI | 5-6 | 6-7 |

EXAMPLE 4

Photochemical stabilization of dyed and undyed polyamide material

Six 100-g strands of polyamide-66 were treated blind with and without additive of 2.5 mg Cu Complex IV and dyed with the combinations of dyestuffs set out in Examples 2 and 3. Treatment proceeded in all cases as described in Example 2.

The yarn was then illuminated in a Xenotest apparatus (see Example 2) for 1000 hours, as laid down in SN-ISO 105-B02, and then checked for breaking strength and stretch according to SNV 197.461.

| Yarn | Breaking Strength (%) | Stretch (%) |
|---|---|---|
| Blind treatment unilluminated | 100 | 100 |
| Blind treatment illuminated | | |
| without Cu—complex | 36 | 60,7 |
| with Cu—complex IV | 90,6 | 96,2 |
| Beige dye illuminated | | |
| without Cu—complex | 74 | 82,7 |
| with Cu—complex IV | 87,5 | 88 |
| Olive dye illuminated | | |
| without Cu—complex | 77 | 84,7 |
| with Cu—complex IV | 85,3 | 89,8 |

Even though the dyestuffs used in the colouring process belong to a class of metal complex dyes that protect the polyamide material from photochemical decomposition, the addition of the Cu complex of Formula IV leads to a significant improvement in the breaking strength of the fibre material.

EXAMPLE 5

Production of the Cu complex of Formula IV (a) Production of the ligands.

0.45 g ethylene diamine, dissolved in 2 ml water, was stirred into a boiling solution of 4.0 g salicylaldehyde sulfonic acid-Na-salt in 75 ml 90% isopropanol. This resulted immediately in a heavy precipitation. This was boiled for a further 15 minutes while refluxing, filtered when hot, and washed with hot 90% isopropanol. The yield was 3.35 g of a light yellow solid substance (94% of the theoretical).

Analysis: $C_{16}H_{14}N_2Na_2O_8S_2$ Calculated: C 40.7; H 3.0; N 5.9. Found: C 40.8; H 3.2; N 5.9.

The substance can also be extracted from the same educts in an aqueous solution.

(b) Metallization

An aqueous solution of 2.5 g copper-II-sulfate was stirred into 25 ml 1-normal caustic soda. The precipitated copper hydroxide was drawn off and then well washed. The filter residue was stirred with 30 ml water while 1 g of the product as in Example 5a was added portion by portion. Stirring was continued for 30 minutes, the filtrate drawn off from the unconverted copper hydroxide and 250 ml ethanol added to the filtrate. The precipitate was drawn off, washed with 90% ethanol, and dried in an Exsiccator. The yield was 0.8 g copper complex of Formula IV as a light violet-coloured powder (64% of the theoretical). The end product contained 4 mol crystal water.

Analysis: $C_{16}H_{20}CuN_2Na_2O_{12}S_2$ Calculated: C 31.7; H 3.3; N 4.6; Cu 10.5. Found: C 32.0; H 3.5; N 5.0; Cu 10.7.

The substance can be salted out from an aqueous solution with household salt or will precipitate as a poorly soluble copper salt by treatment with copper-(II) ions. The compound also results from the copper complex of the salicylaldehyde sulfonic acid-Na-salt described in the literature (M. Calvin, N. C. Melchior JACS 70, 3270-3 (1948)) by conversion with ethylene diamine in boiling diluted alcohol, although the purity is low.

EXAMPLE 6

Production of the copper complex of Formula VI 2.24 parts of the sodium salt of 2-hydroxybenzaldehyde-5-sulfonic acid were dissolved in 20 parts water at 70° C. After the addition of 1.36 parts benzoic acid hydrazide the reaction mixture was kept at 90°-95° C. for one hour, this resulting in a clear, yellow solution of the hydrazone compound, made up as follows:

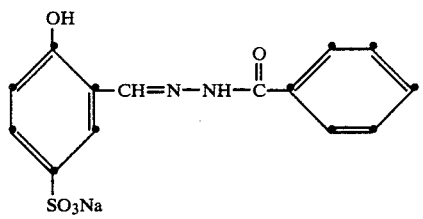

For conversion to the copper complex a solution of 1.7 parts $CuCl_2.2H_2O$ and 4 parts crystallized sodium acetate in 10 parts water was added to the reaction solution that had been obtained and subsequently maintained for 30 minutes at 70°-75° C. The 1:1-copper complex in the form of a greenish-yellow precipitate was completely dissolved to a pH value of 9.0-9.5 by the addition of 2n-sodium hydroxide solution. The yellowish green solution was reduced until dry, this resulting in 7 parts of copper complex in the form of an olive green powder that dissolves readily in water.

Any other copper salt or freshly precipitated copper hydroxide can be used in place of the copper chloride to produce the copper hydroxide.

If 0.60 parts formic acid anhydride or 0.74 parts acetic acid anhydride are used in place of the benzoic acid anhydride to produce the hydrazone compound, analagous 1:1 copper complexes which, when applied to polyamide fibre material display similar stabilizing characteristics, will result.

EXAMPLE 7

Production of the Cu complex of Formula V (a) Production of the Ligands

A solution of 0.25 g o-phenylene diamine in 10 ml 95% isopropanol was added drop by drop over a period of 30 mins to a boiling suspension of 1.21 g salicylaldehyde sulfonic acid-Na-salt in 45 ml 95% isopropanol, while stirring. This was then boiled while refluxing for a further 3 hours. It was then filtered while hot through a pressure suction filter and subsequently washed with boiling 95% isopropanol. The yield was 1.15 g of a light yellow substance (89% of the theoretical). The product contained 2 mol crystal water.

Analysis: $C_{20}H_{18}N_2Na_2O_{10}S_2$ Calculated: C 43.2; H 3.3; N 5.0. Found: C 43.2; H 3.2; N 4.8.

The substance can be produced from the same educts in an aqueous solution and precipitates from the reaction solution by the addition of alcohol.

(b) Metallization

A slurry of freshly precipitated copper hydroxide (from 1.5 g copper-II sulfate as in Example 5b) in 5 ml water was added to the solution of 1 g of product as in Example 7a in 10 ml water. This was stirred for 2 hours, drawn off from the unconverted copper hydroxide, washed with a little water and the filtrate poured into 50 ml ethanol. The precipitate was drawn off, washed with ethanol, and dried in an Exsiccator. The yield was 0.78 g copper complex of Formula V in the form of a dark brown powder (71% of the theoretical) with 2 mol crystal water.

Analysis: $C_{20}H_{16}CuN_2Na_2O_{10}S_2$ Calculated: C 38.9; H 2.6; N 4.5; Cu 10.3. Found C 38.9; H 3.2; N 4.5; Cu 9.7.

The substance also results from the copper complex of the salicylaldehyde sulfonic acid-Na-salt and o-phenylene diamine in boiling 90% ethanol.

EXAMPLE 8

Photostabilization of Polyamide material dyed with various metal complex dyestuffs Six 10-g strands of polyamide-66 were treated with dyes in a laboratory dyeing apparatus at a dye ratio of 1:20; this contained the additives listed in the table, in addition to 2% ammonium sulfate (pH 6.8) and 0.5 g/liter 4-nonylphenol.10 ethylene oxide as a dispersant. This was first processed for 10 minutes at 40° C. and the bath was then heated to 95° C. for 30 minutes. After 10 minutes 2% acetic acid (80%) was added (pH 5.2) and dyeing was continued for an additional 35 minutes at 95° C. The reaction was then cooled to 70° C., the yarn was washed with warm and cold water, and dried in a circulating-air oven at 100° C.

The yarn was illuminated for 200 hours at 83° C. in a Fade-ometer (See Example 1) and then tested for breaking strength according to SNV 197.461.

Results:

| Treatment | Additives | Breaking strength (%) |
|---|---|---|
| 1 | none | 33,1 |
| 2 | 0,05% Cu—complex IV | 82,1 |

| Treatment | Additives | Breaking strength (%) |
|---|---|---|
| 3 | 0,075% Dyestuff 6 | 22,3 |
| 4 | 0,075% Dyestuff 6 | |
| | 0,05% Cu—complex IV | 60,7 |
| 5 | 0,075% Dyestuff 7 | 48,4 |
| 6 | 0,075% Dyestuff 7 | |
| | 0,050% Cu—complex IV | 82,8 |
| Starting material, unilluminated | | 100 |

The dyestuff 6 with the formula

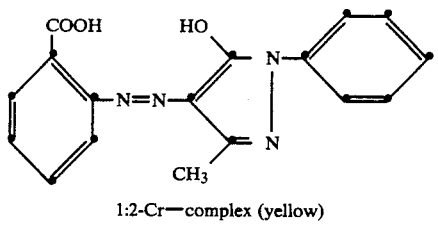

1:2-Cr—complex (yellow)

belongs in the group of dyestuffs that have a negative effect on the light fastness of the polyamide fibres.

The dyestuff 7 with formula

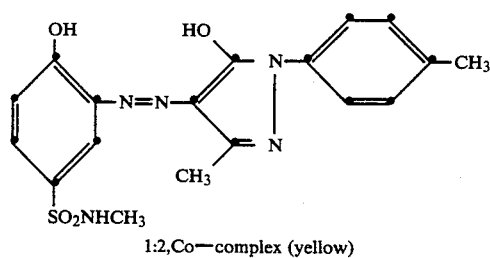

1:2,Co—complex (yellow)

belong, on the other hand, to a group of dyestuffs that protect the polyamide material against photochemical decomposition.

It can be seen clearly from the table for Example 8 that the copper complex IV can check the rapid reduction of the breaking strength, even in the case of dyestuffs that favour the photochemical decomposition of the polyamide fibres.

EXAMPLE 9

Stabilization of polyamide material dyed with dispersion or acid dyestuffs

Six strands of yarn of Polyamide-66 were treated as described in Example 8, illuminated, and tested; the following dyestuffs were used.

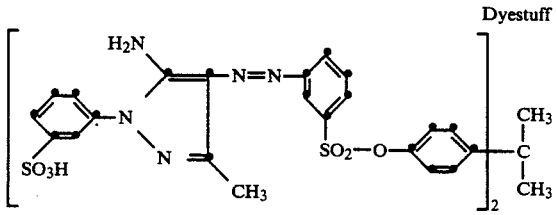

Dyestuff 8

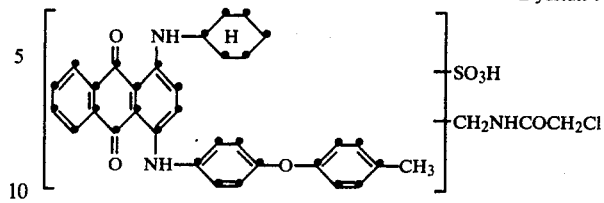

Dyestuff 9

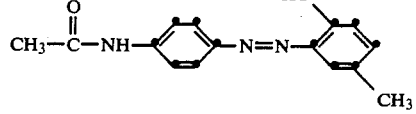

Dyestuff 10

Additions to the dye bath and results obtained.

| Treatment | Additives | Breaking Strength (%) | Stretch (%) |
|---|---|---|---|
| 1 | 0,075% Dyestuff 8 | 39,6 | 68,7 |
| 2 | 0,075% Dyestuff 8 | 72,4 | 97,4 |
| | 0,050% Cu—complex IV | | |
| 3 | 0,075% Dyestuff 9 | 41,3 | 71,2 |
| 4 | 0,075% Dyestuff 9 | 82,0 | 103,5 |
| | 0,050% Cu—complex IV | | |
| 5 | 0,075% Dyestuff 10 | 28,0 | 48,8 |
| 6 | 0,075% Dyestuff 10 | 87,6 | 112,5 |
| | 0,050% Cu—complex IV | | |

The results show that polyamide material coloured with non-metal complex dyestuffs is protected against photochemical decomposition by the addition of a fibre-affinitive, water soluble copper complex.

EXAMPLE 10

Photochemical stabilization of polyamide/polyurethane tricot

Two pieces of tricot, each of 10 g, of 70:30 polyamide-66/Lycra TM, pre-cleaned, were treated in a dyeing apparatus as described in Example 8, at a dye ratio of 1:20 with and without 0.075% Cu complex IV.

Subsequently, the tricot material was illuminated in a Fade-ometer for 80 and 160 hours at 83° C. (see Example 1) and then tested for breaking strength and stretch according to SNV 197.461.

Results

| | Loss of (%) | |
|---|---|---|
| Treatment | Breaking Strength | stretch |
| blind | | |
| unilluminated | — | — |
| 80 hours illumination | 79,9 | 38,3 |
| 160 hours illumination | 94,4 | 52,5 |
| with 0,075% Cu—complex IV | | |
| 80 hours illumination | 27 | 1 |
| 160 hours illumination | 50,4 | 13,3 |

Photochemical decomposition is also delayed to a marked extent in the case of polyamide/polyurethan mixture textiles by the use of a water soluble, fibre affinitive copper complex.

EXAMPLE 11

Photochemical stabilization of dyed polyamide/polyurethane tricot

Four pieces of polyamide 6.6/poyurethane 70/30 were treated as described in Example 8, using the following dyestuffs, with and without Cu complex IV:

Dyeing 1 and 2, with 0.1% dyestuff 10 (see page 24).
Dyeing 3 and 4, with 0.1% dyestuff 11

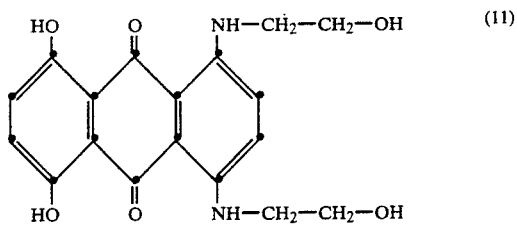
(11)

The dyeing 2 and 3 also contained 0.05% copper complex of Formula IV.

The dyeing was tested by determining the lightfastness (SN–ISO 105–BO2 and DIN 75,202) (provisional), and the breaking strength and stretch (according to SNV 198.461) after 150 hours of illumination in a Fadeometer at 83° C.

Results

| Treatment | Additives | Light fastness | | after 150 hrs. illumination at 83° | |
|---|---|---|---|---|---|
| | | Xenon | Fakra | Breaking strength (%) | Stretch (%) |
| 1 | 0,1% Dyestuff 10 | 6 | 5 | 6,7 | 42,1 |
| 2 | 0,1% Dyestuff 10 + 0,05% Cu—complex IV | 6–7 | 5–6 | 54,8 | 79,8 |
| 3 | 0,1% Dyestuff 11 | 4–5 | 4–5 | 7,1 | 47,1 |
| 4 | 0,1% Dyestuff 11 + 0,05% Cu—complex IV | 6 | 5–6 | 41,7 | 72,7 |
| 0 | untreated, unilluminated | | | 100 | 100 |

The addition of the Cu complex results in good photochemical stabilization of the fibre material and improved light fastness.

EXAMPLE 12

Production of the copper complex of Formula IV 268 g Bis-salicylidene-ethylene diamine were added over a period of 2 minutes to 747 g 21.4% oleum, whereupon the substance went into solution exothermically (approximately 130° C.). This was heated for a further 1½ hours to approximately 105° C. and stirred until the reaction mass thickened. After cooling to 50° C. 3 liters of water were added and the mixture was adjusted slowly to pH 7.5 with 30% caustic soda, this resulting in an internal temperature of 73°–75° C. as a result of the exotherm, and everything went into solution A 60° C. solution of 200 g copper acetate monohydrate in 1.5 liters water was added and the solution was once again adjusted to pH 7.5 with 30% caustic soda and then allowed to cool to room temperature. The precipitate was isolated by pressure filtration, washed with 5% sodium sulfate solution, and dried in a vacuum at 70° C. and conditioned in air for 15 hours (whereupon it takes up crystal water). The yield was 534.5 g of violet-blue compound IV which, according to analysis, contains 5.25% sodium sulfate (pure yield 85%); the product is pure enough for most applications.

In order to remove the sodium sulfate that was added, a 10 g sample of the raw product was stirred into 60 ml. ln Caustic soda, drawn off, washed with ethanol until neutral; after air drying, the yield was 9.0 g violet-blue crystals of Formula IV, containing 3 mol crystal water.

$C_{16}H_{18}CuN_2Na_2O_{11}S_2$ Calculated: C 32.7; H 3.1; Cu 10.8; N 4.7. Found: C 32.4; H 3.1; Cu 10.6; N 4.9.

EXAMPLE 13

Copper complex of the N,N'-Bis[1-(2-hydroxy-5-sulfophenyl)-ethylidene]-ethylene diamine (di-sodium salt).

14.8 g N,N'-Bis-(1-(2-hydroxyphenyl)-ethylidene)-ethylene diamine was introduced within a period of 1 minute into 37 g 21.6% oleum, whereupon it dissolved exothermically (approximately 150° C.). This was maintained for 1 hour at a temperature of approximately 105° C., and then cooled to room temperature; 150 ml water were added to it and it was then adjusted slowly to a pH value of 10.0 with 30% caustic soda and stirred for 5 hours at 60° C. After cooling, it was drawn off, and the residue washed with 2 n caustic soda until sulfate-free, when it was neutralized with ethanol. The filter residue was dissolved in 270 ml water, drawn off from the undissolved impurities, and 900 ml ethanol added to the filtrate; the precipitated product was drawn off, dried in an Exsiccator, and conditioned overnight in air (during which time it absorbed water of crystallization). The yield was 7.1 g violet-bluish pink crystals that contain 3 mol crystal water.

$C_{18}H_{22}CuN_2Na_2O_{11}S_2$ Calculated: C 35.1; H 3.6; Cu 10.3; N 4.5. Found: C 35.4; H 3.4; Cu 10.2; N 4.5.

EXAMPLES 14 to 26

One proceeds analogously to Example 12, although in place of the bisalicylidene-ethylene diamine one uses the bisazomethine of the aldehydes and diamines set out in the following table, whereupon one obtains the corresponding copper complexes. The sulfo groups are in each instance arranged in the p-position of the OH groups.

| Example | Aldehyde | Diamine |
|---|---|---|
| 14 | 2-Hydroxy-3-chlor-benzaldehyde | Ethylenediamine |
| 15 | 2-Hydroxy-3-methoxy-benzaldehyde | Ethylenediamine |
| 16 | 2-Hydroxybenzaldehyde | 1,2-Diaminopropane |
| 17 | 2-Hydroxybenzaldehyde | 1-Phenylethylendiamine |
| 18 | 2-Hydroxybenzaldehyde | cis-1,2-Diaminocyclohexane |
| 19 | 2-Hydroxybenzaldehyde | trans-1,2-Diaminocyclohexane |
| 20 | 2-Hydroxybenzaldehyde | 1,3-Diaminopropane |
| 21 | 2-Hydroxybenzaldehyde | 2,2-Dimethyl-1,3-diaminopropane |
| 22 | 2-Hydroxybenzaldehyde | 2-Hydroxy-1,3-diaminopropane |
| 23 | 2-Hydroxybenzaldehyde | Bis-(3-aminopropyl)amine |
| 24 | 2-Hydroxybenzaldehyde | 1,2-Diaminobenzene |
| 25 | 2-Hydroxybenzaldehyde | 1,2-Diaminobenzene-4-carboxylic acid |
| 26 | 2-Hydroxybenzaldehyde | 1,2-Diaminobenzene-4-carboxylic acid |

EXAMPLE 27

N,N'-bis-(2-hydroxy-5-sulfo-benzylidene)-ethylene diamine-di-Na-salt 0.9 g ethylene diamine is allowed to run slowly into a boiling solution of 8 mg sulfosalicyalidehyde-Na-salt in 200 ml 90% isopropanol. This is boiled for 5 minutes while refluxing, filtered whilst hot, hot washed with 90% isopropanol, yielding after drying 6.85 g of a light yellow solid substance.

$C_{16}H_{14}N_2Na_2S_2$ Calculated: C.40.7; H 3.0; N 5.9. Found: C 40.5; H 3.3; N 5.9.

EXAMPLE 28

One proceeds as in Example 27, although instead of ethylene diamine one uses an equivalent quantity of o-phenylene diamine and obtains N,N'-bis-(2-hydroxy-5-sulfo-benzylidene)-o-phenylene diamine-di-Na-salt.

EXAMPLE 29

Cu complex of the N,N'-bis-(2-hydroxy-5-sulfo-benzylidene)-o-phenylene diamine-di-Na-salt.

6 mmol of moist copper hydroxide, freshly precipitated from aqueous copper sulfate solution with excess sodium hydroxide, were added to a solution of 1.03 g N,N'-bis-(2-hydroxy-5-sulfobenzylidene)-o-phenylenediamine-di-Na-salt (produced as in Example 28) in 10 ml water; the resulting solution was filtered off, and washed until neutral. It was then stirred for 3 hours, drawn off, and the filtrate poured into 50 ml ethanol. The precipitate was drawn off, washed with ethanol and then dried. The yield was 0.8 g of a dark-brown or dark olive yellow solid substance that contains 2 mol crystal water.

$C_{20}H_{16}CuN_2Na_2O_{10}S_2$ Calculated: C 38.9; H 2.6; Cu 10.3; N 4.5. Found: C 38.9; H 3.2; Cu 9.7; N 4.5.

EXAMPLE 30

The same procedure as in Example 29 was used, although N,N'-bis-[1-(2-hydroxy-5-sulfo-phenyl)-ethylidene]-ethylene-diamine-di-Na-salt is used as the bisazomethine, thus obtaining the corresponding copper complex in the form of light violet coloured crystals.

EXAMPLE 31

N,N'-bis-(2-hydroxy-3-sulfo-5-chloro-benzylidene)-ethylenediamine-di-Na-salt 3.37 g N,N'-bis-(2-hydroxy-5-chloro-benzylidene)-ethylenediamine-di-Na-salt were stirred into 9.6 g 25% oleum for one hour at 100° C. This was cooled down, 30 ml water added to it, and enough 30% sodium hydroxide added that the pH value remained constant at 7.5 for a period of several hours. This was drawn off from the precipitated product, washed with water until free of sulfate, and dried. In order to purify it, it was stirred in 100 ml chloroform, drawn off and then dried. The yield was 3.3 g of a yellow solid substance containing 3 mol crystal water.

$C_{16}H_{18}Cl_2N_2Na_2O_{11}S_2$ Calculated: C 32.3; H 3.0; Cl 11.9; N 4.7; S 10.8. Found: C 32.3; H 2.9; Cl 11.7; N 4.8; S 10.8.

EXAMPLE 32

The procedure followed was the same as in Example 31, although N,N'-bis-(2-hydroxy-5-bromo-benzylidene)-ethylene-diamine was used as the diamine, thus obtaining N,N'-bis-(2-hydroxy-3-sulfo-5-bromo-benzylidene)-ethylene-diamine-di-Na-salt.

EXAMPLE 33

Copper complex of the N,N'-bis-(2-hydroxy-3-sulfo-5-bromo-benzylidene)-ethylene-diamine-di-Na-salt 1.35 g of copper acetate monohydrate were dissolved in 20 ml dimethylformamide by gentle heating. 4.52 g of the finely powdered compound obtained as in Example 32 were added and the mixture stirred for one hour. 40 ml of water were then added, whereupon everything initially went into solution, although the product next precipitated out very rapidly. After drawing off, it was washed with water and ethanol and allowed to dry in air. The yield was 4.48 g of a brick red solid substance containing 2 mol crystal water.

$C_{16}H_{14}Br_2CuN_2Na_2O_{10}S_2$ Calculated: C 26.4; H 1.9; Br 22.0; Cu 8.7; N 3.9; S 8.8. Found: C 26.6; H 2.1; Br 21.8; Cu 9.1; N 4.1; S 8.7.

EXAMPLE 34

The procedure here was the same as in Example 33, although the compound obtained as in Example 31 was used as the starting substance and thus one obtained the copper complex of N,N'-bis-(2-hydroxy-3-sulfo-5-chloro-benzylidene)-ethylenediamine-di-Na-salt in the form of a light violet coloured solid substance.

EXAMPLE 35

Copper complex of the N,N'-bis-[2-hydroxy-naphthyl-(1)methylene]-ethylene diamine-di-Na-salt 3.72 g N,N'-bis-[2-hydroxy-naphthyl-(1)methylene]-ethylene diamine were stirred with 10 g 100% sulfuric acid for one hour at 100° C. After cooling, this was poured onto 30 g ice, and adjusted to pH 7.5 with 30% caustic soda. This was then stirred for one hour, drawn off, washed with ice water until free of sulfate, and then dried. The yield was 5.25 g of a yellow solid substance containing 1 mol crystal water.

$C_{24}H_{20}N_2Na_2O_9S_2$ Calculated: C 48.8; H 3.4; N 4.7; S 10.9. Found: C 49.0; H 3.4; N 4.9; S 10.8.

1.67 g copper acetate monohydrate were dissolved in 40 ml dimethylformamide during gentle heating. 4.95 g of the finely powdered above-described yellow solid substance and 4 ml water were added to this and the mixture heated for 2 hours to 100° C. After cooling, it was drawn off, washed with dimethyl formamide and ethanol and air dried. The yield was 5.05 g of an olive yellow substance.

$C_{24}H_{16}CuN_2Na_2O_8S_2$ Calculated: C 45.5; H 2.5; Cu 10.0; N 4.4; S 10.1. Found: C 45.4; H 2.8; Cu 10.0; N 4.5; S 10.0.

EXAMPLE 36

Copper complex of the N,N'-bis-(2-hydroxy-5-sulfo-benzylidene)-3,4-diamino-benzol carboxylic acid-tri-Na-salt A solution of 0.76 g 3.4-diaminobenzoic acid in 5 ml caustic soda was added at 70° C. to a suspension of 2.35 g copper complex of the sulfo-salicylaldehyde-Na-salt in 30 ml ethanol. This was stirred for one hour at 70° C. in a nitrogen atmosphere, cooled, and drawn off. The filter residue was dissolved in 20 ml water and adjusted to be strongly alkaline with a few drops of 1n caustic soda and the precipitated impurities drawn off. The resulting filtrate was poured into 100 ml ethanol, the precipitate filtered off, washed with ethanol until neutral, and air dried. The yield was 2.63 g of a yellow solid substance containing 11 mol crystal water.

$C_{21}H_{33}CuN_2Na_3O_{22}S_2$ Calculated: C 29.3; H.3.9; Cu 7.4; N 3.2. Found: C 29.0; H 3.1; Cu 7.4; N 3.2.

EXAMPLES 37 to 39

The procedure followed was as described for Example 36, although instead of 3,4-diaminobenzoic acid, equivalent quantities of the diamines listed in the following table were used. This resulted in the analogous copper complexes as for Example 36, these being coloured as indicated in the penultimate column and containing the amounts of water of crystallization shown in the final column.

| Example | Diamine | Colour | Mol crystal water pro Mol |
|---|---|---|---|
| 37 | Bis-(3-aminopropyl)-amine | light green | 5 |
| 38 | 1,2-Diaminobenzol | brown-yellow | 2 |
| 39 | 3,4-Diaminobenzolsulfonic-acid | light brown | 7 |

EXAMPLE 40

Cu complex of the N,N'-bis-salicylidene-3,4-diaminobenzoic sulfonic acid-Na-salt A solution of 1.53 g 3,4-diaminobenzene sulfonic acid and 4.1 ml 2n caustic soda in 26 ml 75% ethanol was added at 60° C. to a suspension of 2.44 g salicylaldehyde-Cu-complex in 50 ml ethanol and stirred in a nitrogen atmosphere for 5 hours at 60° C. This was then cooled, drawn off, washed with ethanol and air dried. The yield was 4.0 g of a light browny-yellow solid substance containing 1.5 mol crystal water.

$C_{20}H_{16}CuN_2NaO_{6.5}S$ Calculated: C 47.4; H 3.2; Cu 12.5; N 5.5. Found: C 47.6; H 3.5; Cu 12.2; N 5.4.

EXAMPLE 41

2.24 parts of 2-hydroxybenzaldehyde-5-sulfonic acid in the form of the sodium salt were dissolved in 50 parts water at 70° C. whilst being stirred. After the addition of 1.11 parts semicarbacid-hydrochloride the reaction mixture was adjusted to a constant pH of 7.0 by adding drops of dilute sodium hydroxide solution, and then stirred for one hour at 70° to 75° C. The result was a clear, slightly greenish-yellow solution of the following hydrazone compound:

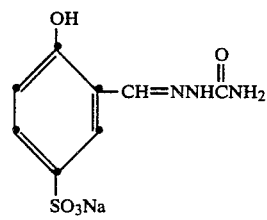

In order to convert this to the corresponding copper complex, a solution of 1.70 parts copper-II chloride dihydrate and 4.0 parts crystallized sodium acetate in 30 parts water was added to the reaction solution and then kept at 70° to 75° C. for 30 minutes. The 1:1 copper complex that precipitated out as a blue-green substance was isolated by filtration and washed with diluted sodium chloride solution. This dissolved in a mixture of water and dimethylformamide with a blue-green colour.

EXAMPLE 42

2.24 parts 2-hydroxybenzaldehyde-5-sulfonic acid in the form of a sodium salt were converted under the conditions described in the foregoing example with 0.91 parts thiosemicarbacid to form the hydrazone compound of the following composition:

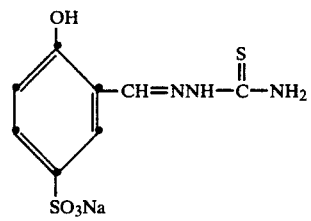

The corresponding 1:1 copper complex can be obtained in the same way as the above-discussed complex and dissolves in water with an olive-brown colour.

What is claimed is:

1. A process for the photochemical stabilization of undyed or dyed polyamide or polyurethane fiber material which comprises treating said material with a water-soluble copper, manganese or nickel complex of a tetradentrate bisazomethine, an acylhydrazone a semicarbazone or a thiosemicarbazone of an aromatic aldehyde or ketone, said complex containing at least one sulfo group.

2. A process for the photochemical stabilization of undyed or dyed polyamide material which comprises treating said material with a water soluble copper, manganese or nickel complex of the formula

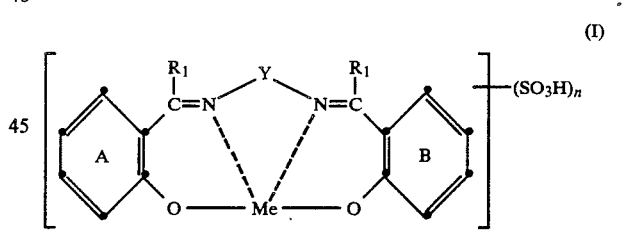

or a salt thereof,
wherein:
$R_1$ is hydrogen; $C_1$-$C_8$ alkyl which is unsubstituted or substituted by halogen, $C_1$-$C_4$-alkoxy, phenyl, carboxyl, hydroxy, cyclohexyl or mono- or dialkyl amino; or aryl which is unsubstituted or substituted by $C_1$-$C_4$-alkyl, $C_1$-$C_4$-alkoxy, halogen, $C_2$-$C_5$-alkanoylamino, nitro, cyano, sulfo or mono- or dialkylamino;

Y is alkylene of 2 to 8 carbon atoms which may be interrupted by oxygen or nitrogen; or arylene which is unsubstituted or substituted by $C_1$-$C_4$-alkyl or $C_1$-$C_4$-alkoxy;

Me is copper, manganese or nickel; and
n is 1, 2 or 3.

3. A process for the photochemical stabilization of undyed or dyed polyamide or polyurethane fiber material which comprises treating said material with a water-soluble copper, manganese or nickel complex of the formula

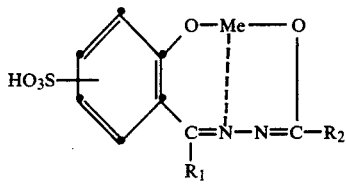

or a salt thereof
wherein:
$R_1$ is hydrogen; $C_1$–$C_8$ alkyl which is unsubstituted or substituted by halogen, $C_1$–$C_4$-alkoxy, phenyl, carboxyl, hydroxy, cyclohexyl or mono- or dialkyl amino; or aryl which is unsubstituted or substituted by $C_1$–$C_4$-alkyl, $C_1$–$C_4$-alkoxy, halogen, $C_2$–$C_5$-alkanoylamino, nitro, cyano, sulfo or mono- or dialkylamino; or $R_2$ is hydrogen; $C_1$–$C_8$ alkyl which is unsubstituted or substituted by halogen, $C_1$–$C_4$-alkoxy, phenyl, carboxyl, hydroxy, cyclohexyl or mono- or dialkyl amino; or aryl which is unsubstituted or substituted by $C_1$–$C_4$-alkyl, $C_1$–$C_4$-alkoxy, halogen, $C_2$–$C_5$-alkanoylamino, nitro, cyano, sulfo or mono- or dialkylamino; and Me is copper, manganese or nickel.

4. A process for the photochemical stabilization of undyded or dyed polyamide or polyurethane fiber material which comprises treating said material with a water-soluble copper, manganese or nickel complex of the formula

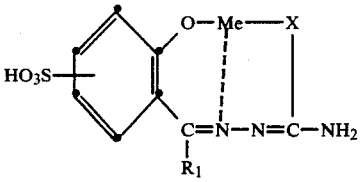

or a salt thereof,
wherein:
$R_1$ is hydrogen; $C_1$–$C_8$ alkyl which is unsbustituted or substituted by halogen, $C_1$–$C_4$-alkoxy, phenyl, carboxyl, hydroxy, cyclohexyl or mono- or dialkyl amino; or aryl which is unsubstituted or substituted by $C_1$–$C_4$-alkyl, $C_1$–$C_4$-alkoxy, halogen, $C_2$–$C_5$-alkanoylamino, nitro, cyano, sulfo or mono- or dialkylamino;

X is oxygen or sulfur; and
Me is copper, manganese or nickel.

5. A process according to claim 1 wherein Me is copper.

6. A process according to claim 1 wherein the metal complex is added directly to the dye bath.

7. A process as according to claim 1 wherein the metal complex is used at such a quantity that 5–200 μg metal are applied for each 1 g polyamide or polyurethane fibre.

8. A process according to claim 1 wherein 10–100 μg of metal are applied on each 1 g polyamide or polyurethane material.

9. The dyed or undyed polyamide or polyurethane fibre material and fibre mixtures prepared by a process as in claim 1.

* * * * *